(12) United States Patent
Kim et al.

(10) Patent No.: US 11,369,383 B2
(45) Date of Patent: Jun. 28, 2022

(54) BAND TIGHTENING APPARATUS FOR BINDING INTESTINE

(71) Applicant: JSR MEDICAL CO., LTD., Daegu (KR)

(72) Inventors: Jae Hwang Kim, Daegu (KR); Chang Young Chae, Gyeongsangbuk-do (KR)

(73) Assignee: JSR MEDICAL CO., LTD., Daegu (KR)

( * ) Notice: Subject to any disclaimer, the term of this patent is extended or adjusted under 35 U.S.C. 154(b) by 0 days.

(21) Appl. No.: 17/265,651

(22) PCT Filed: Jan. 31, 2019

(86) PCT No.: PCT/KR2019/001318
§ 371 (c)(1),
(2) Date: Feb. 3, 2021

(87) PCT Pub. No.: WO2020/032334
PCT Pub. Date: Feb. 13, 2020

(65) Prior Publication Data
US 2021/0307757 A1    Oct. 7, 2021

(30) Foreign Application Priority Data

Aug. 6, 2018  (KR) .......................... 10-2018-0091229

(51) Int. Cl.
*A61B 17/12*    (2006.01)
*A61B 90/00*    (2016.01)
*A61B 17/00*    (2006.01)

(52) U.S. Cl.
CPC ................... *A61B 17/12009* (2013.01); *A61B 2017/00845* (2013.01); *A61B 2090/064* (2016.02)

(58) Field of Classification Search
CPC .... A61B 17/12009; A61B 2017/12018; A61B 17/12013; A61B 17/12; A61F 5/005; A61F 5/0066; B65D 33/165
(Continued)

(56) References Cited

U.S. PATENT DOCUMENTS

| 5,707,378 A | 1/1998 | Ahn et al. |
| 6,676,674 B1 | 1/2004 | Dudai |

(Continued)

FOREIGN PATENT DOCUMENTS

| JP | 2007044503 A | 2/2007 |
| JP | 2007-216014 A | 8/2007 |

(Continued)

OTHER PUBLICATIONS

Office action dated Nov. 4, 2021 from Korean Patent Office in a counterpart Korean Patent Application No. 10-2020-0036293(all the cited references are listed in this IDS.) (English translation is also submitted herewith.).

(Continued)

*Primary Examiner* — Tan-Uyen T Ho
*Assistant Examiner* — Bridget E. Rabaglia
(74) *Attorney, Agent, or Firm* — The PL Law Group, PLLC

(57) ABSTRACT

A band tightening apparatus for binding an intestine with a band according to an embodiment of the present disclosure pulls a holder that fixes a band so that the length of the band wound around the intestine is ideally adjusted. The apparatus can pull the band wound around the intestine so that the length of the band wound around the intestine is ideally adjusted and the apparatus can fix the band with a fixing pin for convenient use.

14 Claims, 22 Drawing Sheets

(58) Field of Classification Search
USPC .......... 606/139, 140, 153; 24/16 PB, 30.5 R, 24/30.5 P, 30.5 S
See application file for complete search history.

(56) References Cited

U.S. PATENT DOCUMENTS

| | | | |
|---|---|---|---|
| 9,555,943 B2 * | 1/2017 | Breen, IV | .............. B65D 63/16 |
| 2007/0167672 A1 | 7/2007 | Dlugos et al. | |

FOREIGN PATENT DOCUMENTS

| | | |
|---|---|---|
| KR | 10-2002-0028506 A | 4/2002 |
| KR | 10-2002-0042634 A | 6/2002 |
| KR | 10-2014-0022270 A | 2/2014 |
| KR | 10-2018-0033983 A | 4/2018 |
| RU | 2 497 469 C2 | 11/2013 |
| WO | WO 2014/007719 A1 | 1/2014 |

OTHER PUBLICATIONS

International Search Report for PCT/KR2019/001318 dated May 14, 2019.
European Search Report For EP 19848559.1 dated Apr. 7, 2022 from European patent office in a counterpart European patent application(all the cited references are listed in this IDS).

* cited by examiner

BAND TIGHTENING APPARATUS FOR BINDING INTESTINE

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2019/001318, filed Jan. 31, 2019, which claims priority to the benefit of Korean Patent Application No. 10-2018-0091229 filed in the Korean Intellectual Property Office on Aug. 6, 2018, the entire contents of which are incorporated herein by reference.

BACKGROUND

Technical Field

The present invention relates to a band tightening apparatus and, more particularly, to a band tightening apparatus for binding an intestine with a band, the apparatus being capable of binding an intestine with a band by ideally adjusting the tension of the band.

Background Art

Colon cancer is a malignant tumor that occurs in the colon and rectum and is mostly adenocarcinoma that occurs specifically in the mucous membrane of the colon. Although most colon cancers are adenocarcinoma, some are squamous cell carcinoma, malignant lymphoma, and malignant sarcoma. Colon cancer occurs due to invasion of cancers in surrounding organs into the large intestine, or metastasis of cancers in other areas to the large intestine. Most of adenocarcinomas develop from benign tumors (polyps) which are adenomas.

These colon cancers can be classified into ascending colon cancer, descending colon cancer, and rectal cancer depending on the location of the lesion. The incidence of descending colon cancer is higher than that of ascending colon cancer, and the incidence of rectal cancer is higher than that of descending colon cancer. This is because the influence of pancreatic enzymes on the large intestine decreases from the ascending colon to the descending colon.

In general, colon cancer surgery involves incisions at upper and lower ends of a lesion to cut away the lesion, connection of normal areas, and suturing. However, leakage occurring at the anastomosis site may cause serious complications after surgery and may threaten the patient's life. In addition, it causes long-term anastomotic stricture and seriously degrades the patient's quality of life.

The incidence of leakage after colon cancer surgery is reported to be very high (for example, about 8% to 25%). In addition, unlike colon cancer patients who are capable of normal bowel movements after surgery and recovery, in the case of rectal cancers which most frequently occur, since a large area adjacent to the anus is removed through surgery even though the anus remains, rectal cancer patients suffer impaired bowel activity after surgery and recovery.

In order to reduce negative effects of such an anastomosis leakage, colostomy is usually performed. However, colostomy has a problem in that the patient has to carry a colostomy bag where feces collect at all times due to a risk of leakage of stools due to peristalsis of the large intestine. In addition, patient's daily life activities are limited and leaking stools cause odor.

The management of a stoma resulting from colostomy is very cumbersome and uncomfortable. Above all, many patients suffer from extreme mental pain due to the odor caused by leaked stool, the prejudice of people around them, the limitation of daily life activities, and discomfort when wearing clothes. That is, the management of the stoma lowers the quality of life.

In order to solve the problems, an artificial intestinal tract for diverting stool away from a bowel is used.

A conventional artificial intestinal tract is composed of an intestinal tube and a pair of fixation tubes. The artificial intestinal tract is inserted into the bowel of a patient, and the fixation tubes and the intestinal tract are fastened with an intestinal band.

The most important thing in the use of the artificial intestine is to stably fix the artificial intestinal tract to the patient's intestinal tract, to prevent necrosis of the intestinal tract, and to easily remove the artificial intestinal tract after a certain period of time.

To this end, research on biodegradable bands is being actively conducted.

The biodegradable band is provided between the fixation tubes. The band must stably fix the artificial intestinal tract, needs to not be significantly deformed or loosened by peristalsis, and needs to be appropriately tensioned not to cause intestinal necrosis when it is fixed to the intestine.

A conventional biodegradable band is installed such that a band having an appropriate length and being made of a biodegradable material is manually wound around an intestine between fixation tubes. An end of the band is cut and fixed by a band installation machine.

However, with the conventional method, it is not easy to supply a band with a suitable length depending on a patient, that is, a band with a proper tension, and it is difficult to quickly supply a suitable band to a patient during surgery.

SUMMARY

Accordingly, the present invention has been made in view of the problems occurring in the related art and a first objective of the present invention is to provide a band tightening apparatus for binding an intestine with a band, the apparatus being capable of supplying a band having an appropriate tension to a patient.

A second objective of the present invention is to provide a band tightening apparatus for binding an intestine with a band, the apparatus being capable of tightening a band around an intestine such that a smooth blood flow in the wall of the intestine can be maintained, by maintaining a distance between the band and a fixing pin that fixes the band.

A third objective of the present invention is to provide a band tightening apparatus in which a fixing pin can be separated from a holder by a preset suitable tension and the fixing pin is positioned at a position at which the band has an optimum tension. Thus, a doctor can easily cut away a residual portion of the band.

In order to accomplish the first through third objectives, the present invention provides a band tightening apparatus for binding an intestine with a band, the apparatus including: a band having an elongated shape; a fixing pin including a passage-providing member into which one end of the band passes; a holder configured to be assembled with and disassembled from the fixing pin and configured to fix one end of the band; and a pulling member configured to move the holder, in which a second end of the band is moved such that the band surrounds an intestine, is moved through the passage-providing member of the fixing pin, and is fixed to the holder.

The pulling member may pull the holder toward the inside thereof so that a distance between the fixing pin and the band is adjusted to be a preset reference distance.

The pulling member may have a guide member for guiding movement of a hook.

The holder may have pin fixing portions at respective side ends thereof, and the pin fixing portions may release the fixing pin when a pulling force is applied to the fixing pin by the pulling member.

The holder may include band fixing portions that fix the respective side edges of the band.

The fixing pin may include a fixing protrusion that restricts a direction in which the band moves such that the band moves only toward the inside of the pulling member.

The reference distance may range from 3 mm to 7 mm.

The guide member may have a slot-shaped opening linearly extending in a longitudinal direction of the guide member, a portion of the guide member may be exposed through the opening, and the exposed portion may be a curved surface.

The guide member may be an elongated member such that the hook moves along the longitudinal direction of the guide member.

The pulling member may have a pressure sensor installed therein to measure a pulling force generated by the hook to pull the holder.

An inner surface of the guide member may not be uniform in height.

The pin fixing portions fix the fixing pin by pressing the fixing pin from respective sides. When the holder is pulled toward the inside of the holder and the pulling force is applied to the fixing pin, the pin fixing portions are separated from the fixing pin.

The band has notches at respective side edges thereof, each of the band fixing portions has a protrusion corresponding to one of the notches, and the band is fixed by the protrusions fitted into the respective notches.

The protrusion may protrude from the inner surface of the fixing pin and may have an inclined surface. The protrusion allows the band to move toward the inside of the pulling member and prevents the band from moving outward from the pulling member.

The band tightening apparatus for binding an intestine with a band, according to the present invention, can apply a band maintaining an optimum tension to a patient. The apparatus maintains the distance between the band and the fixing pin that fixes the band, thereby optimally tightening the band such that intestinal relaxation and contraction and smooth blood circulation are allowed. In addition, when a predetermined pulling force is applied to the fixing pin, the fixing pin can be easily separated from the holder so that a doctor can easily cut away a redundant portion of the band, which is present outside the fixing pin.

DETAILED DESCRIPTION

Figure 1:
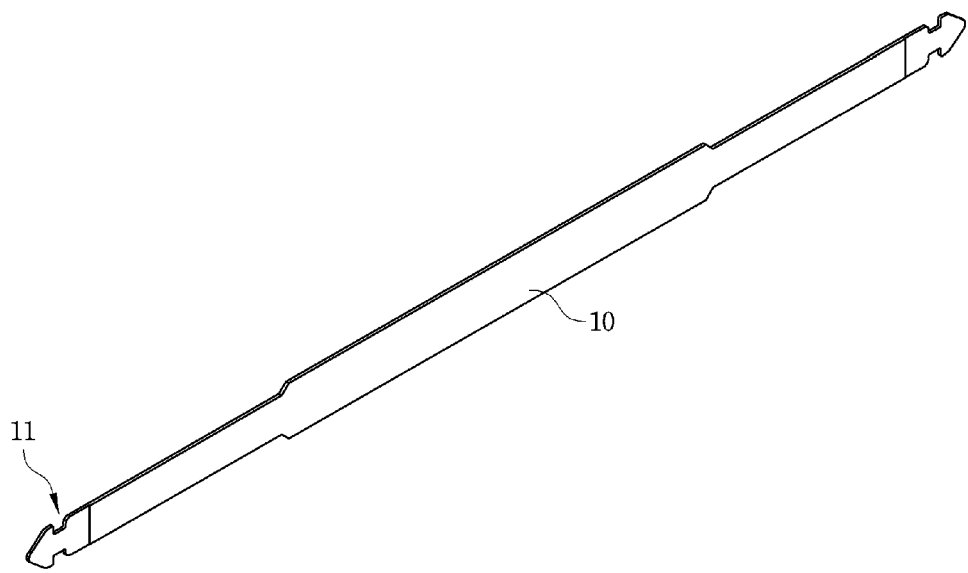
FIG. 1 is a perspective view illustrating a band according to one embodiment of the present invention.

It should be noted that the terms and words used in the specification and the claims should not be construed as being limited to ordinary meanings or dictionary definitions but should be construed in a sense and concept consistent with the technical idea of the present disclosure, on the basis that the inventor can properly define the concept of a term to describe its invention in the best way possible.

It will be further understood that the terms "comprises", "includes" or "has", when used in this specification, specify the presence of an element, but do not preclude the presence or addition of one or more other elements unless the context clearly indicates otherwise. The terms "~ part", "~ unit", "module", "stage", "apparatus" and the like mean a unit for processing at least one function or operation and may be implemented by hardware, software, or both.

The terms used in embodiments of the present invention will be first briefly described, and the embodiments will be then described in detail.

As the terms used in the embodiments of the present invention, general terms currently widely used are selected while considering functions in the present invention. However, the terms may vary depending on the intention of an ordinarily skilled person in the field, judicial precedents, and the emergence of new technologies, etc. In addition, there may be terms arbitrarily selected by the inventor(s). In this case, the meaning thereof will be described in detail in the description of the present invention. Therefore, the term used in the present invention should not be defined not on the name of a simple term but should be defined on the basis of the meaning of the term and the entire contents of the present invention.

Terms used in the specification, "first", "second", etc. can be used to discriminate one component from another component, but the order or priority of the components is not limited unless specifically stated. These terms are used only for the purpose of distinguishing a component from another component. For example, a first constitutive element may be referred as a second constitutive element, and the second constitutive element may be also referred to as the first constitutive element. Moreover, the term "and/or" includes any and all combinations of one or more of the associated listed items.

As used herein, the singular forms "a", "an", and "the" are intended to include the plural forms as well unless the context clearly indicates otherwise.

It will be further understood that the terms "comprises", "includes", or "has" when used in this specification specify the presence of stated features, regions, integers, steps, operations, elements and/or components, but do not preclude the presence or addition of one or more other features, regions, integers, steps, operations, elements, components and/or combinations thereof.

In addition, in one embodiment of the present invention, the module or unit performs at least one function or operation, and may be implemented with hardware, software, or a combination of hardware and software. In addition, a plurality of modules or units may be integrated into at least one module or unit and may be implemented as at least one processor except for modules or units that need to be implemented with specific hardware.

When an element is described as being "connected to", "combined with", or "coupled to" another element, it should be understood that the element may be connected to, combined with, or coupled to another element directly or with another element interposing therebetween Throughout the specification, examples of a band 10 include a long band, an auxiliary band, a biodegradable strip, a biodegradable band, and the like.

Throughout the description herein, the band 10 is implemented with a long band, an auxiliary band, a biodegradable strip, a biodegradable band, or the like. Alternatively, the band 10 may be implemented with a combination of a long band and an auxiliary band. When the band 10 is implemented with a combination of a long band and an auxiliary band, the long band and the auxiliary band are combined to each other by a fixing hook so as not to be separated from each other. When the band is a combination of a long band and an auxiliary band, the auxiliary band is disposed to come into contact with the outer surface of an intestine.

The long band is made of a woven fabric, and is required not to be loosened when it is wound around the intestine. The long band is required not to be deformed by the peristalsis of the large intestine and to have an optimum tensile strength. The long band is made of a biodegradable material so that it can be biologically decomposed after a certain period of time and is configured not to damage the surface of the wall of the large intestine. The long band is usually of a mesh type that is woven with a biodegradable suture.

The auxiliary band is made of a polymer material such as polyurethane and is made of a slippery and transparent material. The long band and the auxiliary band are made of a material that automatically breaks when a tensile stress applied to the bands exceeds a predetermined value.

Hereinbelow, exemplary embodiments of the present invention will be described in detail with reference to the accompanying drawings.

Figure 2:
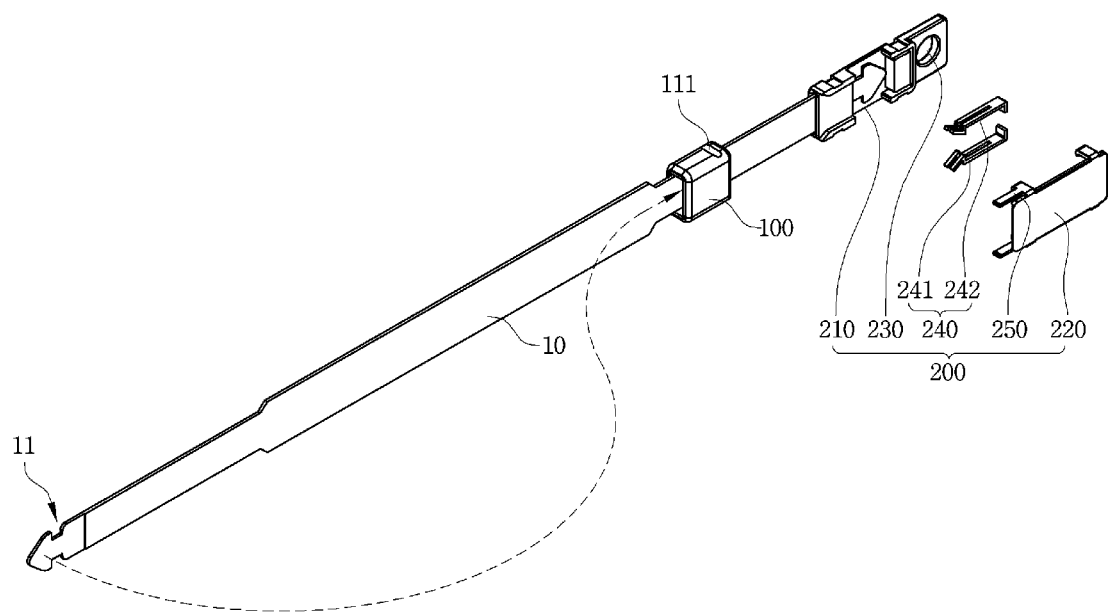
FIG. 2 is an exploded perspective view illustrating a band, a fixing pin, and a holder according to one embodiment of the present invention.

FIG. 1 is a perspective view illustrating a band according to the present invention, and FIG. 2 is an exploded perspective view illustrating the band, a fixing pin, and a holder according to the present invention.

Referring to FIGS. 1 and 2, a band 10 has an elongated shape. The band 10 has notches 11 at respective side edges thereof. Here, the notches 11 provided at the respective side edges of the band 10 may have an arbitrary shape. One end of the band 10 is fixed and the other end of the band 10 is moved such that the band 10 is wound around an intestine.

A fixing pin 100 includes a passage-providing member 120 through which one end of the band 10 passes. Specifically, a second end of the band 10 passes through the passage 120. That is, the second end of the band 10 is moved in a circumferential direction of the intestine so that the band 10 is wound around the intestine and is then passed through the passage of the passage-providing member 120.

A holder 200 is configured to be assembled with and disassembled from the fixing pin 100.

The holder 200 includes pin fixing portions 250 formed at respective side edges thereof. The pin fixing portions 250 are made of an elastic material. The pin fixing portions 250 fix the fixing pin 100 by pressing the respective sides of the fixing pin 100.

When the holder 200 is pulled and thus the pulling force is applied to the fixing pin 100, the pin fixing portions 250 perpendicularly press the fixing pin 100, thereby locking the fixing pin 100.

When a force of pulling the holder 200 is stronger than a force that the pin fixing portions 250 press the fixing pin 100, the pin fixing portions 250 are separated from the respective side surfaces of the fixing pin 100 so that the holder 200 can be released from the fixing pin 100.

The side surfaces of the fixing pin 100, which are pressed by the pin fixing portions 250, are provided with respective recesses 111 that are shaped to correspond to the respective pin fixing portions 150. Thus, the pin fixing portions 250 can be easily separated.

The holder 200 is configured to fix the first end or the second end of the band 10. That is, after the second end of the band 10 is moved in a circumferential direction of the intestine such that the band 10 is wound around the outer surface of the intestine, the second end of the band 10 is passed through the passage of the passage-providing member 120 of the fixing pin and is then fixed to the holder 200.

The holder 200 includes band fixing portions 240 that respectively fastens the sides of the band 10. Specifically, the holder 200 is composed of a first holder case 210 and a second holder case 220, and the band fixing portion 240 is provided inside the holder 200.

Each of the band fixing portions 240 has a protrusion corresponding to one of the recesses 11 of the band 10. The protrusions are inserted into the respective recesses 11 so that the band 10 is locked by the band fixing portions 240.

Each of the band fixing portions 240 is composed of a first band fixing portion 241 and a second band fixing portion 242. Each of the first and second band fixing portions 241 and 242 has a protrusion corresponding to one of the recesses 11 of the band 10. As described above, since each of the band fixing portions 240 is composed of the first band fixing portion 241 and the second band fixing portion 242, the band 10 can be securely locked.

The holder 200 has a loop portion 230 into which a hook 330 to be described later is to be hooked. The loop 230 is shaped to correspond to the shape of the hook 330. The loop 230 may be formed in a second portion of the holder 200 rather than a first portion into which the band 10 is inserted.

Figure 3:
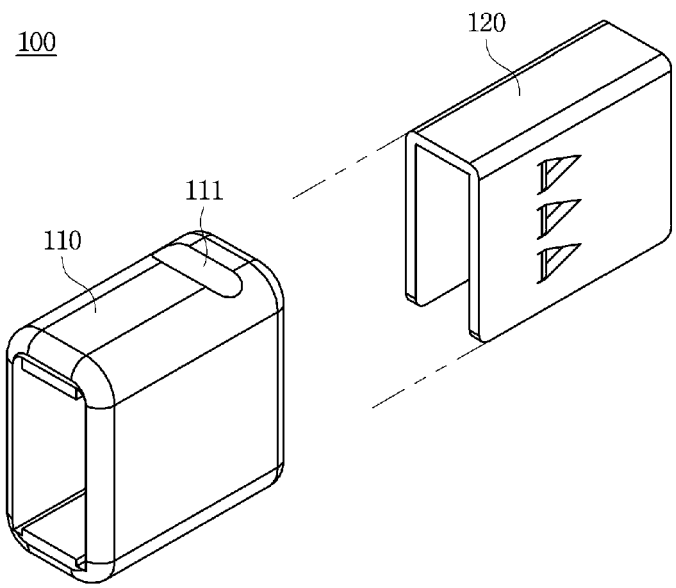
FIG. 3 is an exploded perspective view illustrating the fixing pin according to one embodiment of the present invention.
Figure 4:
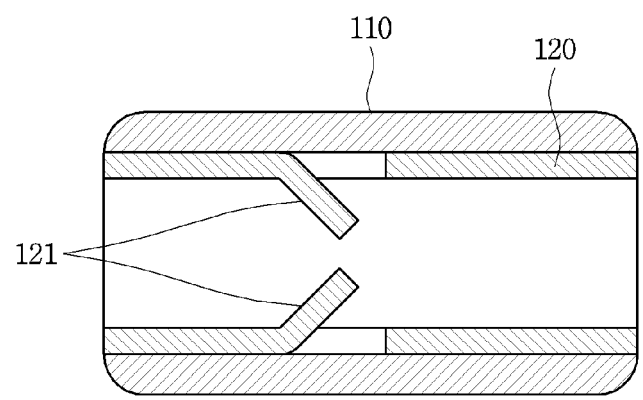
FIG. 4 is a cross-sectional view illustrating the fixing pin according to one embodiment of the present invention.

FIG. 3 is an exploded perspective view illustrating the fixing pin according to one embodiment of the present invention, and FIG. 4 is a cross-sectional view illustrating the fixing pin according to one embodiment of the present invention.

Referring to FIGS. 3 and 4, the fixing pin 100 includes a pin case 110 and a passage-providing member 120. The pin case 110 has recesses 111 at respective side surfaces thereof. The recesses 111 are formed to correspond to the pin fixing portions 250, respectively.

The passage-providing member 120 is inserted into the fixing pin 110. The passage-providing member 120 has a passage through which the band 10 to passes.

In addition, the inner surface of the passage-providing member 120 is provided with fixing protrusions 121 that restricts a direction in which the band 10 moves. That is, the fixing protrusions 121 allow the band 10 to move only in one direction.

The fixing protrusions 121 are formed to protrude from the inner surface of the passage-providing member 120 and are inclined. That is, the fixing protrusions 121 are formed such that the band 10 moves over the inclined surfaces of the fixing protrusions 121 when the band 10 moves in one direction.

However, when the band 10 moves over the inclined surfaces of the fixing protrusions 121 and moves in the reverse direction, the protrusions 121 prevent the band 10 from moving in the reverse direction.

Thus, the fixing protrusions 121 restrict the direction of movement of the band 10 so that the band 10 moves only toward the inside of the pulling member 200 but does not move toward the outside of the pulling member 200.

Figure 5:
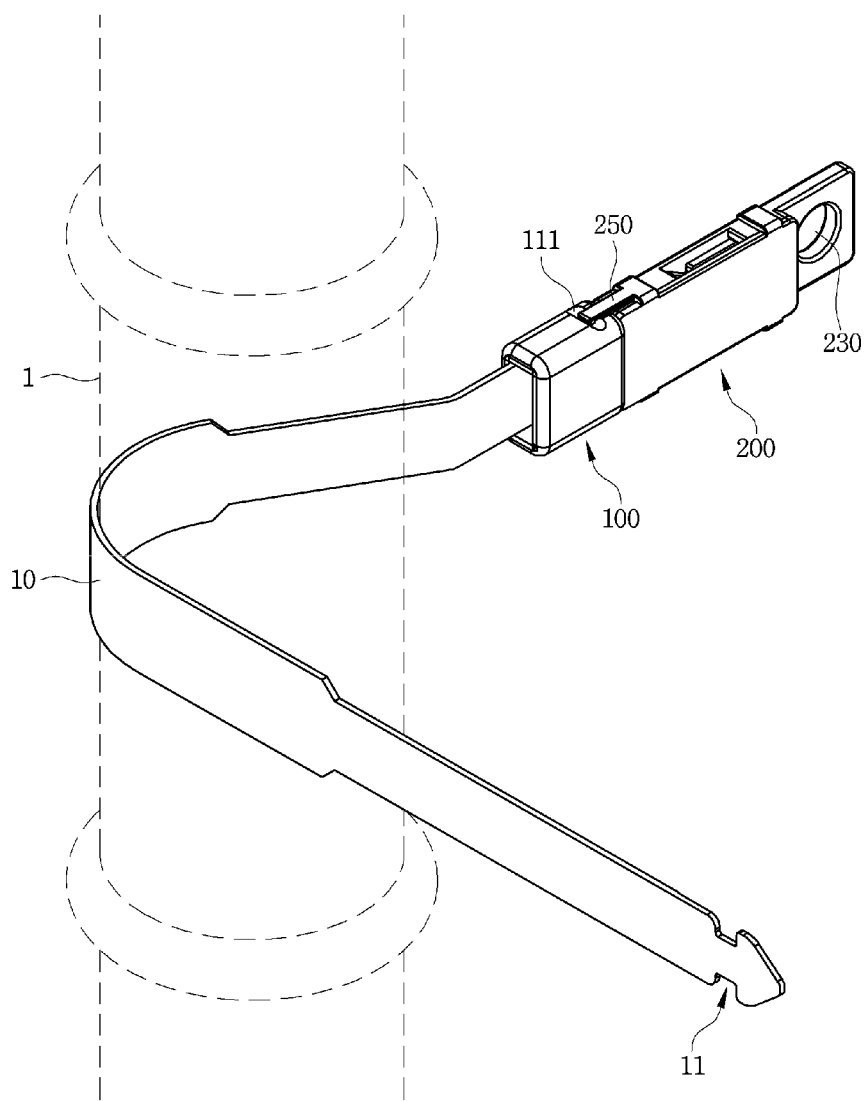
FIG. 5 is a view illustrating an exemplary operation according to one embodiment of the present invention.
Figure 6:
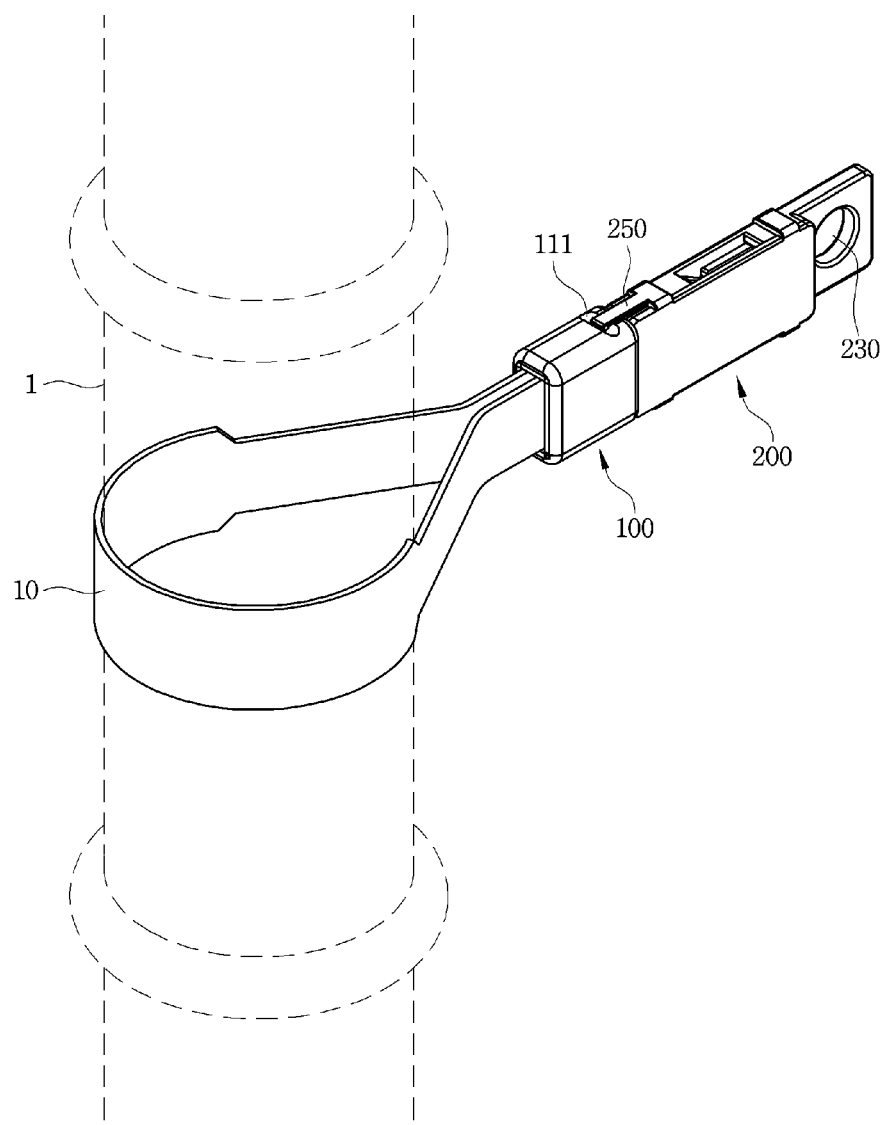
FIG. 6 is a view illustrating an exemplary operation according to one embodiment of the present invention.

FIG. 5 is a view illustrating an exemplary operation according to one embodiment of the present invention, and FIG. 6 is a view illustrating an exemplary operation according to one embodiment of the present invention.

Referring to FIGS. 5 and 6, a first end of the band 10 is passed through the fixing pin 100 and is then fixed to the holder 200, and a second end of the band 10 is moved along the outer surface of an intestine 1 in a circumferential direction so that the band 10 is wound around the intestine 1 and is then fixed to the holder 200.

Figure 7:
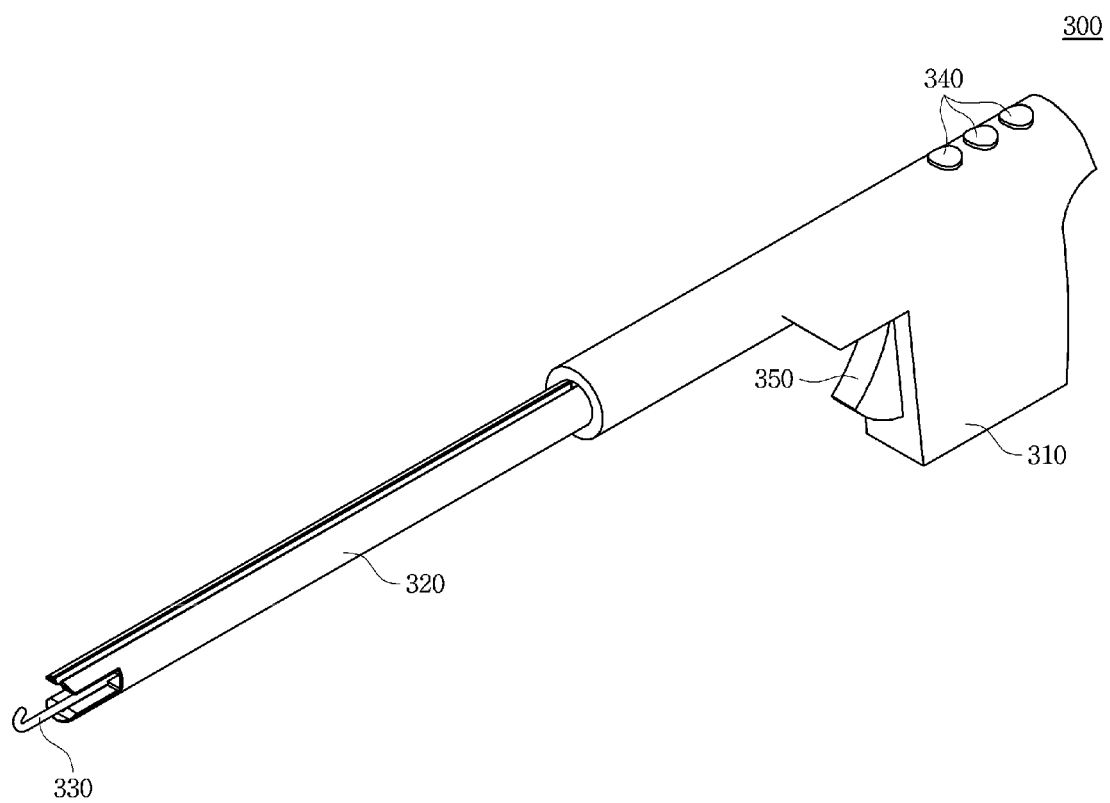
FIG. 7 is a perspective view illustrating a pulling member in one embodiment of the present invention.
Figure 8:
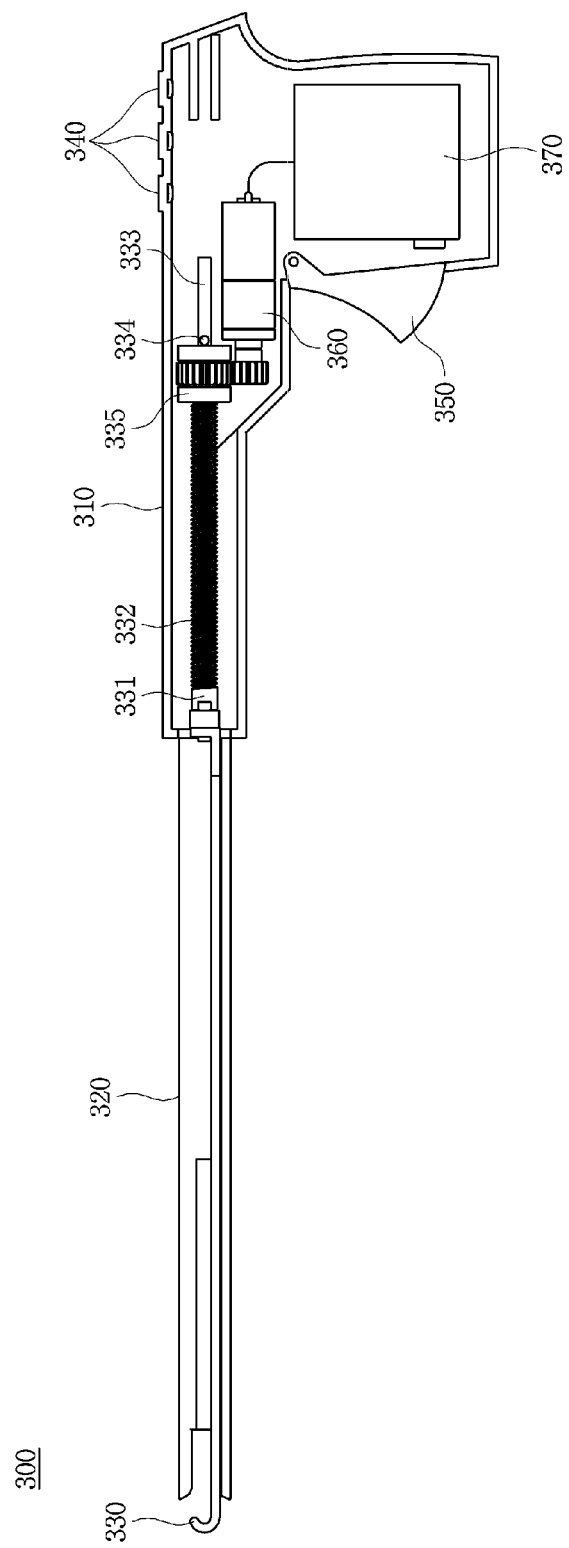
FIG. 8 is a cross-sectional view illustrating the pulling member according to one embodiment of the present invention.
Figure 9:
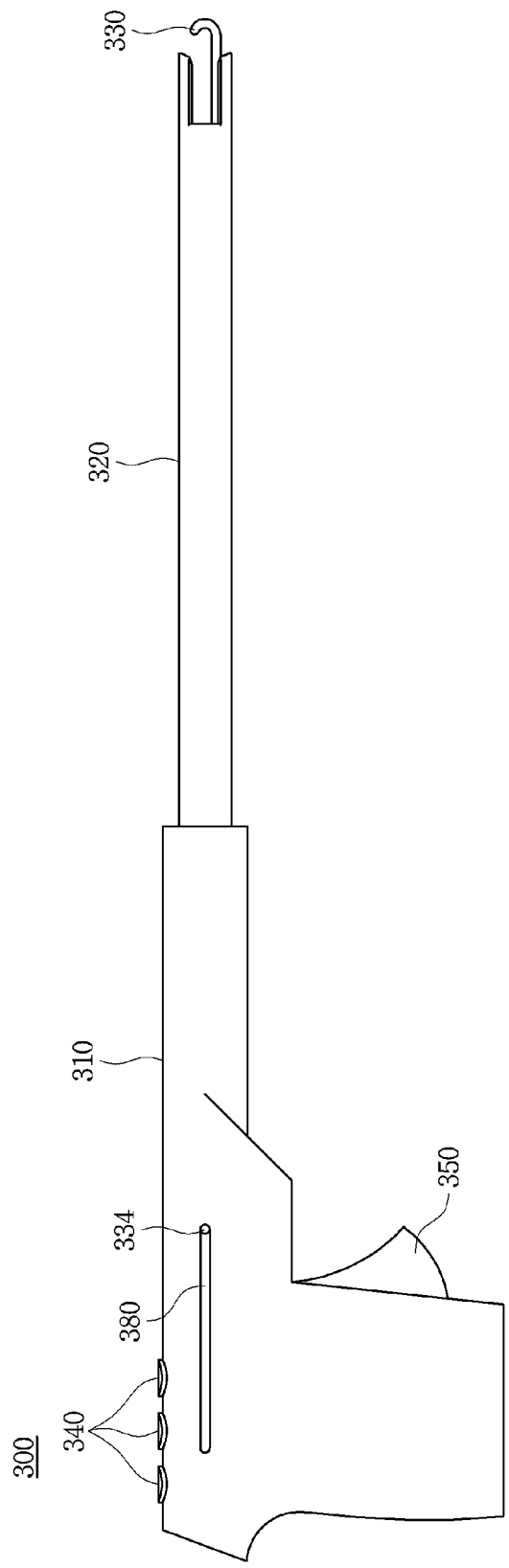
FIG. 9 is a side elevation illustrating the pulling member according to one embodiment of the present invention.
Figure 10:
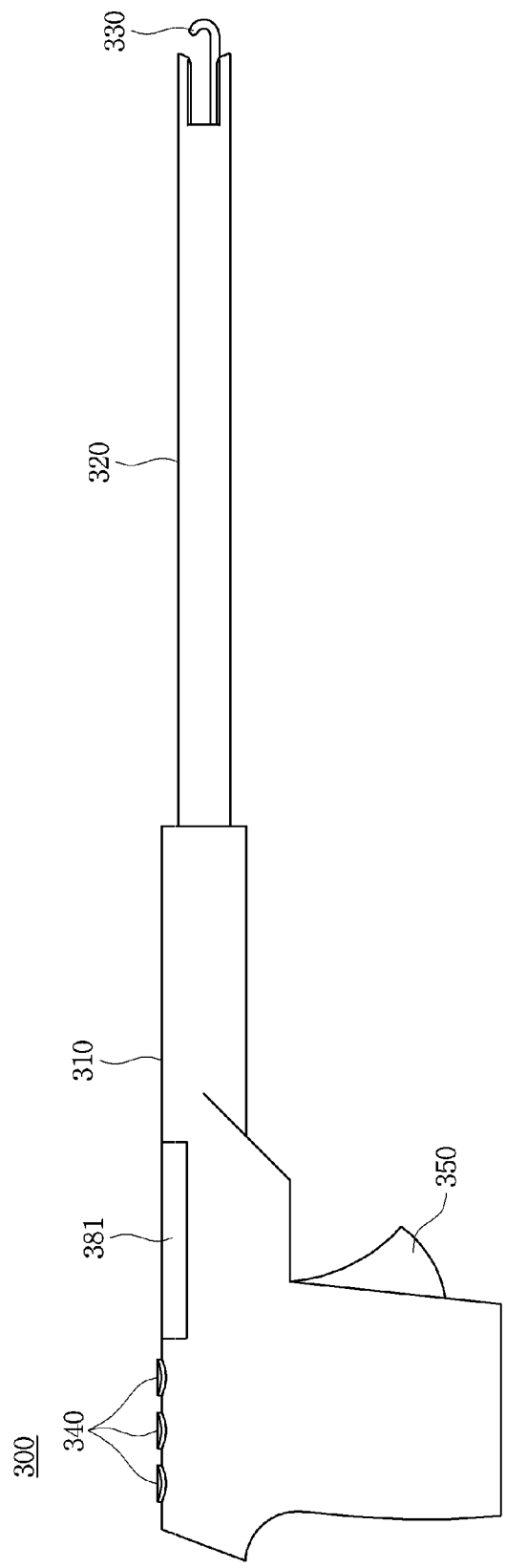
FIG. 10 is a cross-sectional view illustrating a pulling member according to another embodiment of the present invention.
Figure 11:
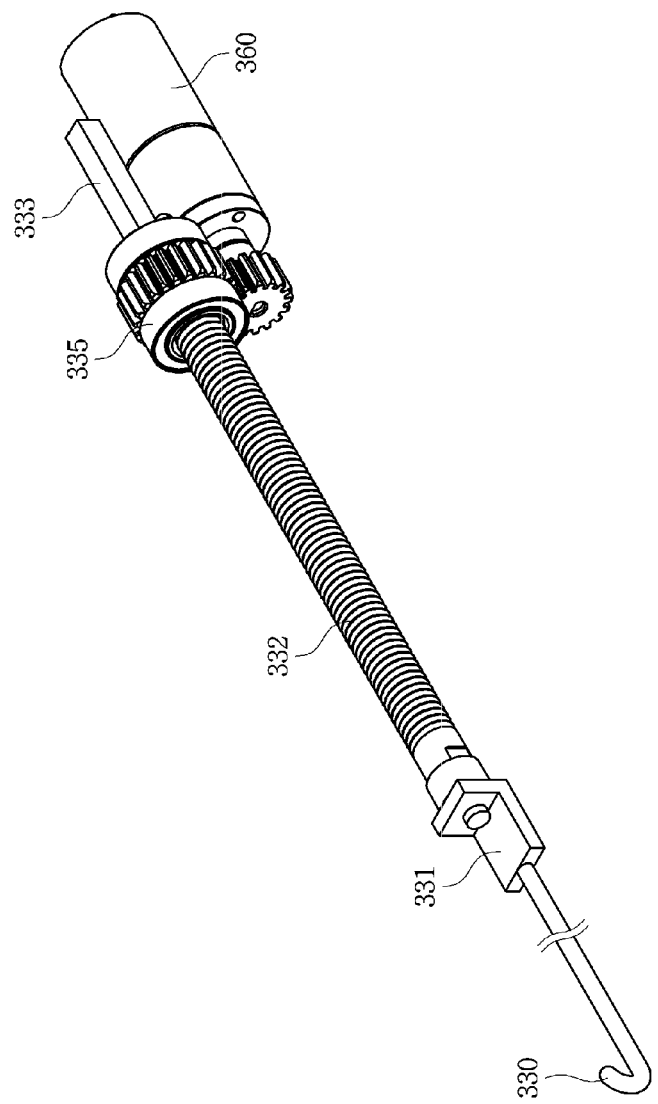
FIG. 11 is a perspective view illustrating a hook, a pressure sensor, a threaded portion, a gear, a release-preventing portion, and a force generation portion, according to one embodiment of the present invention.

FIG. 7 is a perspective view illustrating a pulling member according to one embodiment of the present invention, FIG. 8 is a cross-sectional view illustrating the pulling member according to one embodiment of the present invention, FIG. 9 is a side elevation illustrating the pulling member according to one embodiment of the present invention, FIG. 10 is a side elevation illustrating a pulling member according to another embodiment of the present invention, and FIG. 11 is a perspective view illustrating a hook, a pressure sensor, a threaded portion, a gear, a release-preventing portion, and a force generation unit, according to the present invention.

Referring to FIGS. 7 through 11, a pulling member 300 enables the holder 200 to move into the pulling member 300 by pulling the holder 200. The pulling member 300 pulls the fixing pin 100 when the fixing pin 100 is combined with the holder 200.

The pulling member 300 includes a body 310 and a guide member 320.

The pulling member 300 pulls the holder 200 toward the pulling member so that a distance between the fixing pin and the band 10 is adjusted to a preset reference distance.

For example, the reference distance ranges from 3 mm to 7 mm and is preferably 5 mm. That is, an allowable error of the reference distance ranges from ±2 mm to ±5 mm.

More specifically, this reference distance is set to be equal to the outer diameter of a bowl management system for fecal diverting, which is installed in a bowel (intestinal tract).

That is, since the outer diameter of the bowel (intestinal tract) changes depending on the outer diameter of the bowel management system installed in the bowel (intestinal tract), the reference distance needs to be equal to the outer diameter of the bowel management system.

More specifically, when the outer diameter of the bowel management system installed in the bowl (intestinal tract) is 22 mm, and when a force of 1000 gmN to 2000 gmN is applied, the distance (i.e., reference distance) between the fixing pin 100 and the band 10 is set to be in a range of 3 mm to 7 mm.

The reference distance is increased or decreased according to the outer diameter of the bowel management system.

The reference distance is determined such that the intestine can be completely surrounded by the band. When the reference distance is determined, intestinal relaxation and contraction and blood circulation need to be considered.

When applying a predetermined pulling force is applied to the holder 200 by the pulling member 300, the pull member 300 can return a hook 330 to be described later to a default position without requiring an additional force. This operation will be described below.

The body 310 and the guide member 320 of the pulling member 300 form a housing. The body 310 and the guide member 320 are separate members to be combined to form the housing. Alternatively, the body 310 and the guide member 320 are integrated.

The guide member 320 is an elongated member along which the hook 330 moves.

The guide member 320 has an elongated opening extending in a longitudinal direction. The surface exposed through the elongated opening of the guide member 320 is a curved surface. The curved surface is designed to conform to the shape of an intestine because a curved surface of the band 10 comes into contact with the bowel when the pulling member 300 pulls the holder 200 toward the inside of the pulling member 300.

That is, since the outer surface of the intestine is a curved surface, the outer surface of the band 10 is also curved. When one surface of the guide member 320, which is to come into contact with the outer surface of the band 10, is curved, it is possible to prevent the outer surface of the wall of the intestine or the outer surface of the band 10 from being damaged.

An end of the hook 330 is rounded. The end of the hook 330 is hooked into a loop 230. When the end of the hook 330 is curved, a second side of the guide member 320 in a longitudinal direction is open to form a guide line for movement of the hook.

In addition, an operation unit 340 is formed on the outer surface of the body 310 to manipulate the pulling member 300. Thus, an electrical signal can be generated as necessary and a push button is used to switch on and off a power supply unit 370. When a user pushes the push button 350, the pulling member 300 pulls the holder 200 toward the inside of the pulling member 300.

In addition, a window 380 is formed at a portion of the outer surface of the body 310, and the window 380 is formed to be transparent. The user can visually check the movement of the release-preventing protrusion 334 through the window 380. Thus, the user can check how hard the holder 200 is pulled by the pulling member, i.e., by which length the band 10 is pulled by the pulling member 300.

The outer surface of the body 310 is also provided with a display unit 381. The value of the pulling force of the pulling member 300 is displayed on the display unit 381. That is, by displaying the pulling force applied to the holder 200 is measured by the pressure sensor 331 to be described below, and the measured force is displayed on the display unit. Thus, the user can conveniently use the apparatus while checking the pulling force applied to the band.

In addition, information of an electrical signal generated from the operation unit 340 according to the user's intention is also displayed on the display unit 381.

When the pulling force applied to the holder 200 through manipulation of the operation unit 340 is increased or decreased, an increase or decrease in the pulling force is displayed on the display unit 381. In addition, the state of charge (SoC) of the battery in the power supply unit 370 is displayed on the display unit 381.

With the use of the operation unit 340, at least one of the magnitude and duration of the pulling force to be applied to the holder 200 is set, and a pulling force according to the magnitude and duration that are preset is applied to the holder 200.

That is, the holder 200 and the fixing pin 300 can be separated by the force that is preset, and the band 10 can be wound around the outer surface of the intestine according to the magnitude and duration of the force.

The hook 330 is installed in the guide member 320, and the pressure sensor 331, a threaded portion 332, a release-preventing portion 333, a release-preventing protrusion 334, a gear 335, a for generating portion 360, and a power supply unit 370 are installed in the body 310.

Here, the hook 330 is formed to be fitted into the loop 230 of the holder 200. The pressure sensor 331 measures the pulling force when the hook 330 pulls the holder 200. Here, the pressure sensor 331 is disposed in a place where the pulling force of the hook 330 can be measured when the hook 330 pulls the holder 200.

That is, in the present specification, for convenience of description, the pressure sensor 331 is disposed between the hook 330 and the thread portion 332. However, the arrangement of the pressure sensor 331 is not limited to a position between the hook 330 and the threaded portion 3320.

The hook 330 may be disposed on a first surface of the pressure sensor 331.

The threaded portion 332 may be disposed on a second surface of the pressure sensor 331. In addition, the gear 335 may be disposed on the outer surface of the thread portion 332, and the release-preventing portion 333 is disposed on one side of the thread portion 332.

The inner surface of the gear 335 is provided screw threads corresponding to the screw threads of the threaded portion 332. The outer surface of the gear 335 is provided gear teeth so as to correspond to a force transfer unit of the force generation unit 360.

That is, the force generation unit 360 generates a driving force when it is powered by the power supply unit 370 and transfers the generated driving force to the gear 335 through the force transfer unit. The gear 335 rotates by the transferred driving force and transfers a driving force to the threaded portion 332. The thread portion 332 pulls the hook 330 using the transferred driving force, thereby applying the pulling force to the holder 200. With the structure described above, it is possible to apply the pulling force to the holder 200 on the basis of the driving force generated by the force generation unit 360.

In addition, the surface of the release-preventing portion 333 is provided with the release-preventing protrusion, thereby preventing the gear 335 from escaping. That is, by preventing the excessive movement of the gear 335, it is possible to prevent the hook 330 from applying an excessive force to the holder 200.

When the hook 330 applies a force to the holder 200, the pressure sensor 331 detects a pressure corresponding to the preset force. In this case, the force generation unit 360 generates a force to move the hook 330 to an initial position (default position).

The gear 335 and the thread portion 332 receive the force for moving the hook 330 to the default position, and the hook 330 returns to the default position due to the force.

That is, the hook 330 can apply a preset pulling force to the holder 200. When the hook 330 applies a preset pulling force to the holder 200, additional force is not applied to the holder 200 by the hook 330. The hook 330 can be returned to the default position at which the hook 330 is located before applying the force to the holder 200.

Therefore, a doctor can conveniently cut the band 10.

Figure 12:
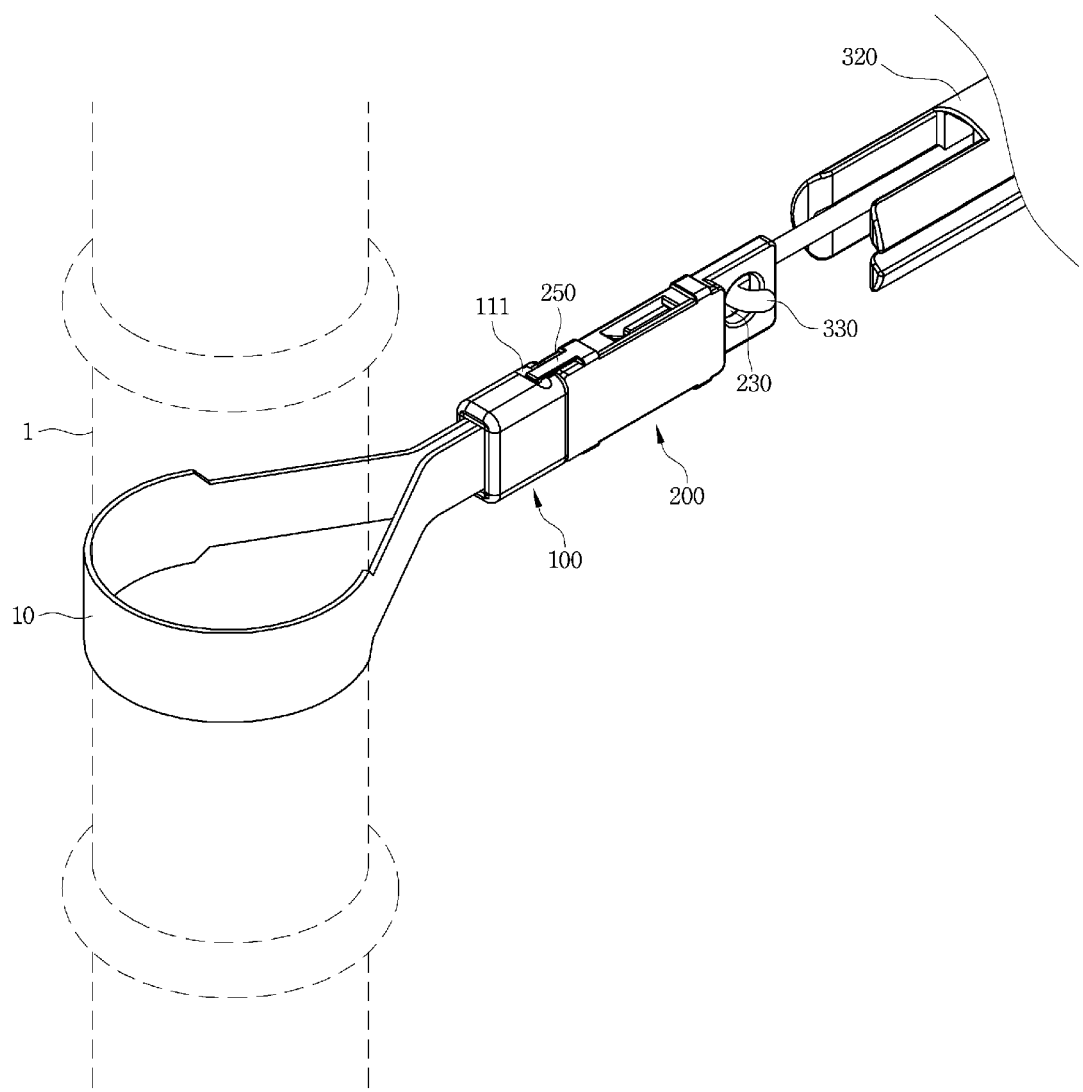
FIG. 12 is a view illustrating an exemplary operation according to one embodiment of the present invention.
Figure 13:
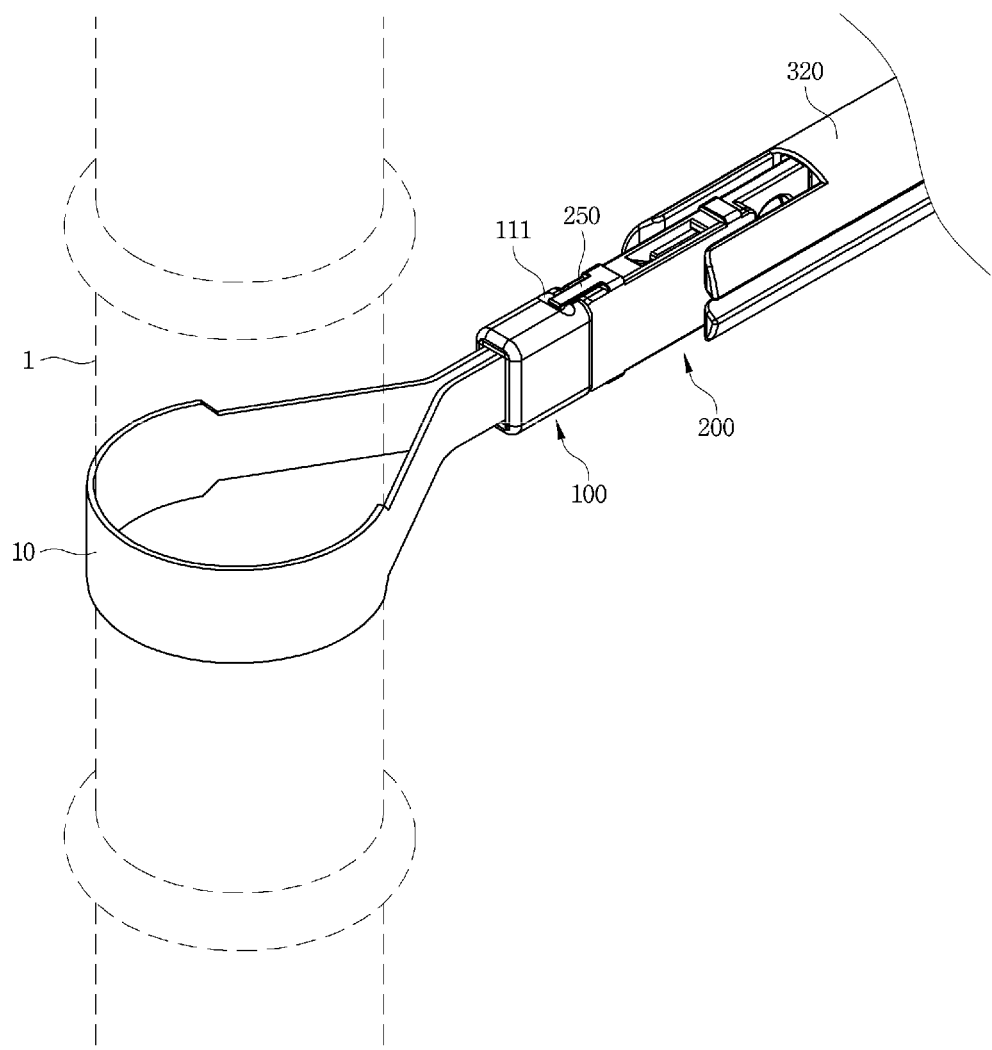
FIG. 13 is an operational view illustrating one embodiment of the present invention.
Figure 14:
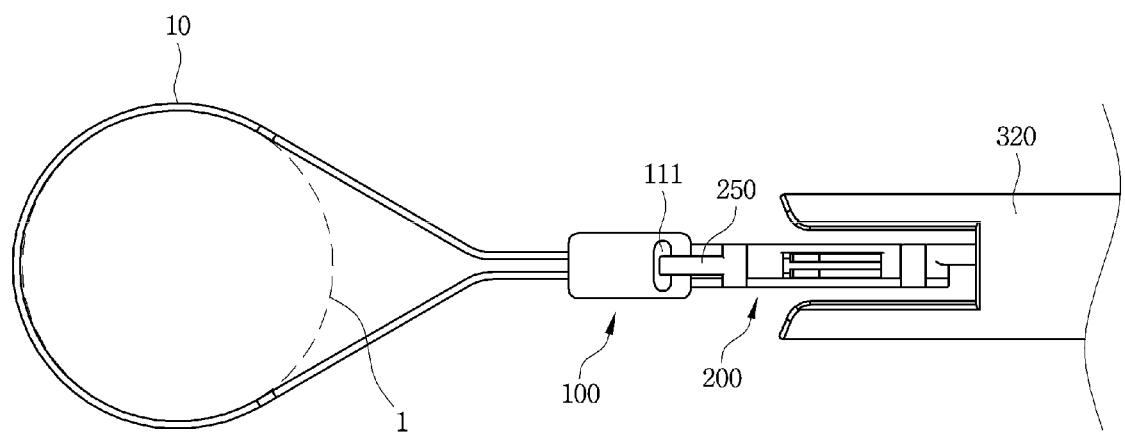
FIG. 14 is a plan view illustrating an exemplary operation according to one embodiment of the present invention.

FIG. 12 is a view illustrating an exemplary operation according to one embodiment of the present invention, FIG. 13 is a view illustrating an exemplary operation according to one embodiment of the present invention, and FIG. 14 is a plan view illustrating an exemplary operation according to one embodiment of the present invention.

Specifically, FIG. 12 illustrates a state in which the band 10 is wound around the intestine 1 and one end of the band 100 is passed through the fixing pin 100 and is fixed to the holder 200. It is further illustrated that the hook 330 is hooked into the loop of the holder 200. FIG. 13 illustrates a state in which the hook 330 hooked into the loop 230 applies a pulling force to the holder 200, thereby pulling the band 10, the fixing pin 100, and the holder 200. FIG. 14 is a plan view illustrating a state in which the hook 330 hooked into the loop 230 applies a pulling force to the holder 200, thereby pulling the band 10, the fixing pin 100, and the holder 200.

Figure 15A:
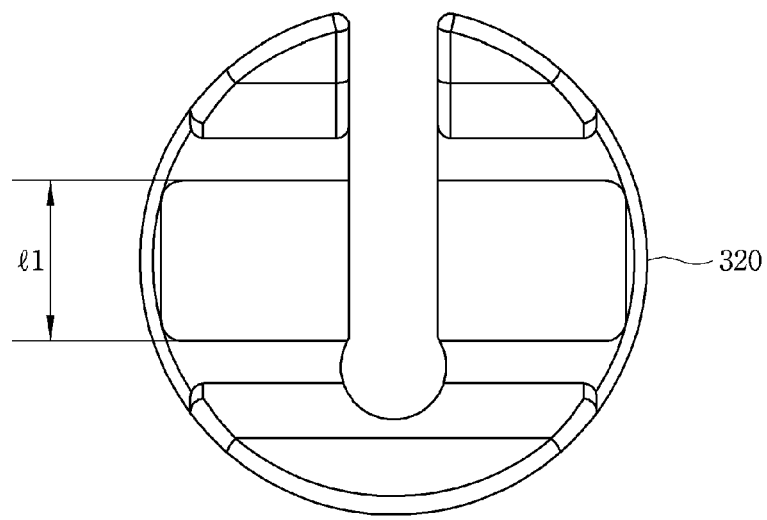
FIGS. 15a, 15b, and 15c are views illustrating comparison of the heights of regions of an inner surface of a guide member, the height of a fixing pin, and the height of a holder, according to one embodiment of the present invention.
Figure 15B:
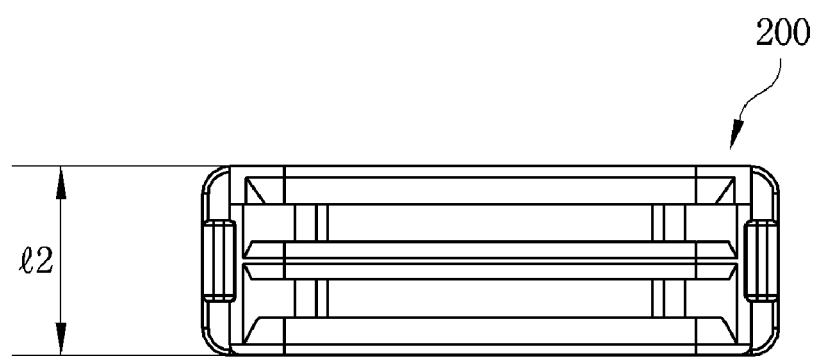
Figure 15C:
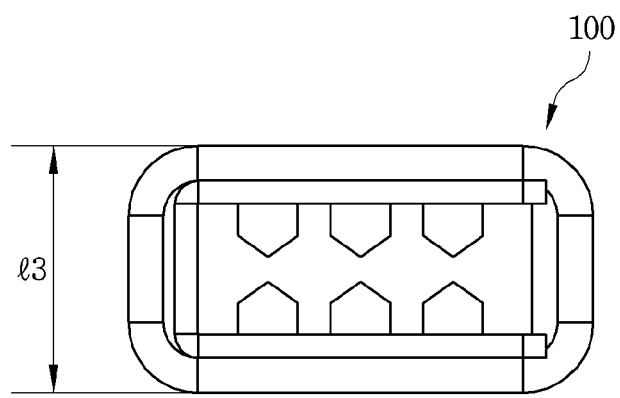
Figure 16:
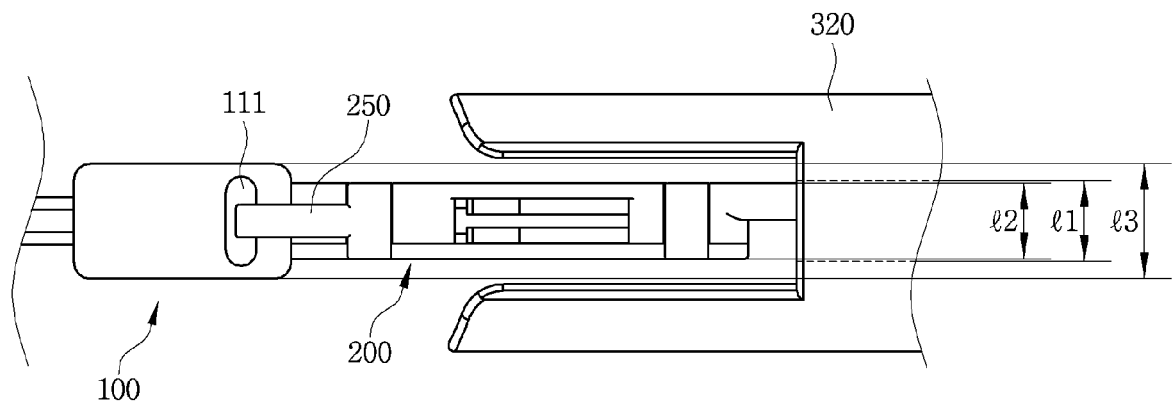
FIG. 16 is a plan view illustrating comparison among the heights of regions of an inner surface of a guide member, the height of a fixing pin, and the height of a holder, according to one embodiment of the present invention.

FIGS. 15a, 15b, and 15c are views illustrating comparison among the heights of regions of an inner surface of a guide member, the height of a fixing pin, and the height of a holder, according to one embodiment of the present invention; FIG. 16 is a plan view illustrating comparison among the heights of regions of an inner surface of a guide member, the height of a fixing pin, and the height of a holder, according to one embodiment of the present invention; and FIG. 17 is a view illustrating a state in which the fixing pin is released from the pin fixing portions, according to one embodiment of the present invention.

Referring to FIGS. 15a to 17, FIG. 15a and FIG. 16 illustrate a case where there are height differences on the inner side of the guide member 320, and 11 denotes the height of an accommodation space formed in the guide member 320. In addition, 12 in FIG. 15b and FIG. 16 denotes the height of the holder, and 13 in FIG. 15c and FIG. 16 denotes the height of the fixing pin 100.

That is, since the value of the height of the holder 200 is less than the value of the height of the accommodation space in the guide member 320 that has a height difference on the inner surface thereof, the holder 200 can be received in the accommodation space defined in the guide member 320. However, since the value of the height of the fixing pin 100 is greater than the value of the height of the accommodation space, the fixing pin 100 cannot be received in the accommodation space. That is, the fixing pin is stopped by a stepped portion of the inner surface of the guide member 320.

Figure 17:
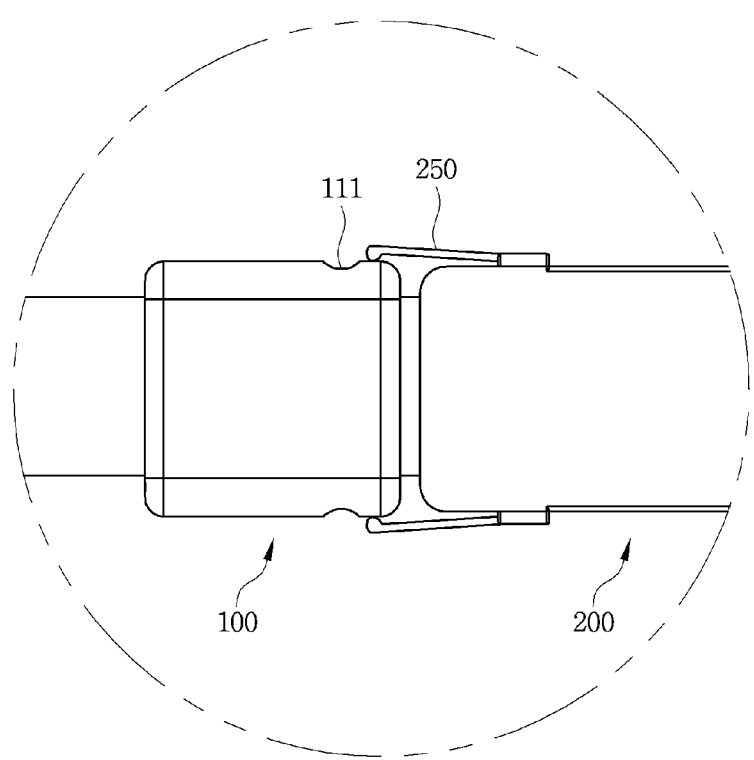
FIG. 17 is a view illustrating a state in which the fixing pin is released from the pin fixing portions, according to one embodiment of the present invention.

FIG. 17 is an enlarged view illustrating a state in which the pin fixing portion 250 is separated from the recess 111 of the fixing pin. In addition, when the hook is hooked into the loop 230 and the hook 330 pulls the holder 200 toward the inside of the pulling member 300, the pulling force is applied to the band 10, the fixing pin 100, and the holder 200.

In this case, the band 10, the fixing pin 100, and the holder 200 will be moved into the guide member 320, and the holder 200 is introduced into the accommodation space of the guide member 320. However, since the fixing pin 100 cannot be received in the accommodation space, it is block by the stepped portion. When the force of pulling the fixing pin 100 toward the inside of the pulling member is continuously applied, the force becomes stronger than the force of perpendicularly pressing the side surfaces of the fixing pin 100 by the pin fixing portion 250. At this time, the pin fixing portion 250 are separated from the respective recesses 111 so that the fixing pin 100 and the holder 200 are separated from each other.

Figure 18:
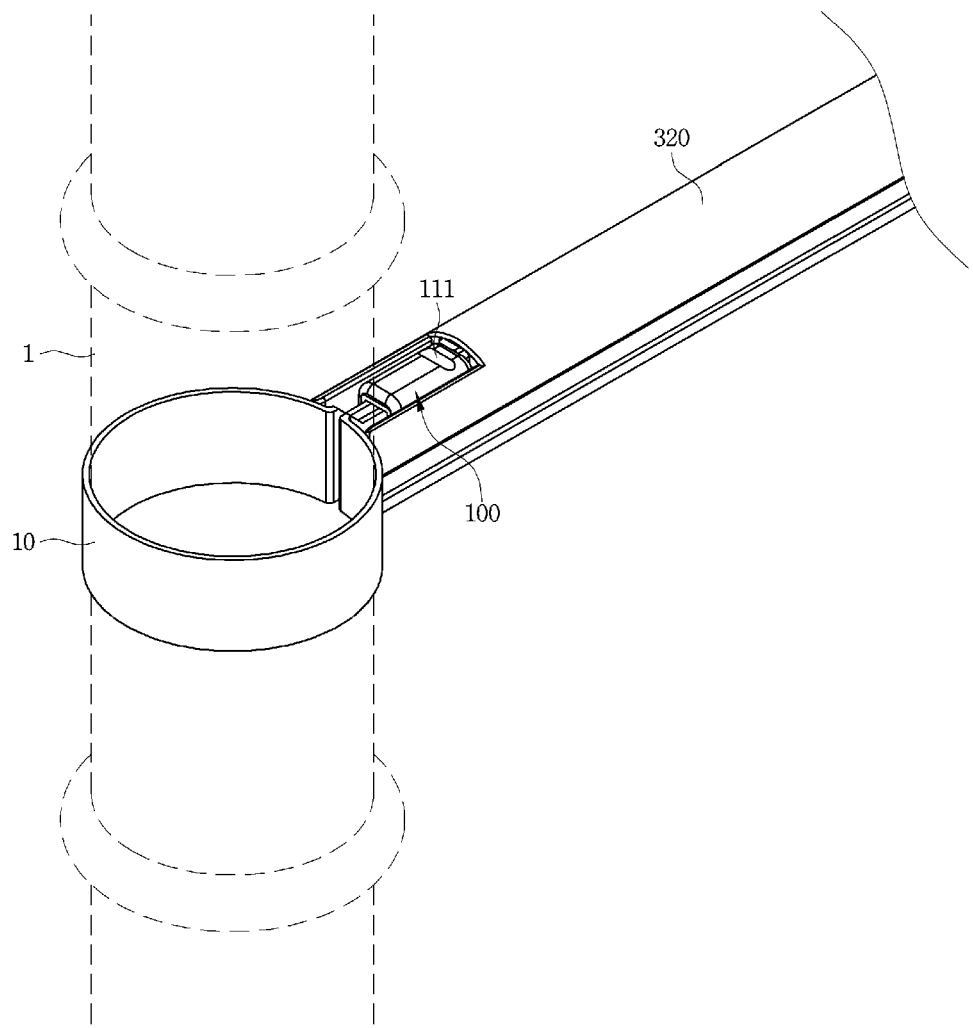
FIG. 18 is a view illustrating an exemplary operation according to one embodiment of the present invention.
Figure 19:
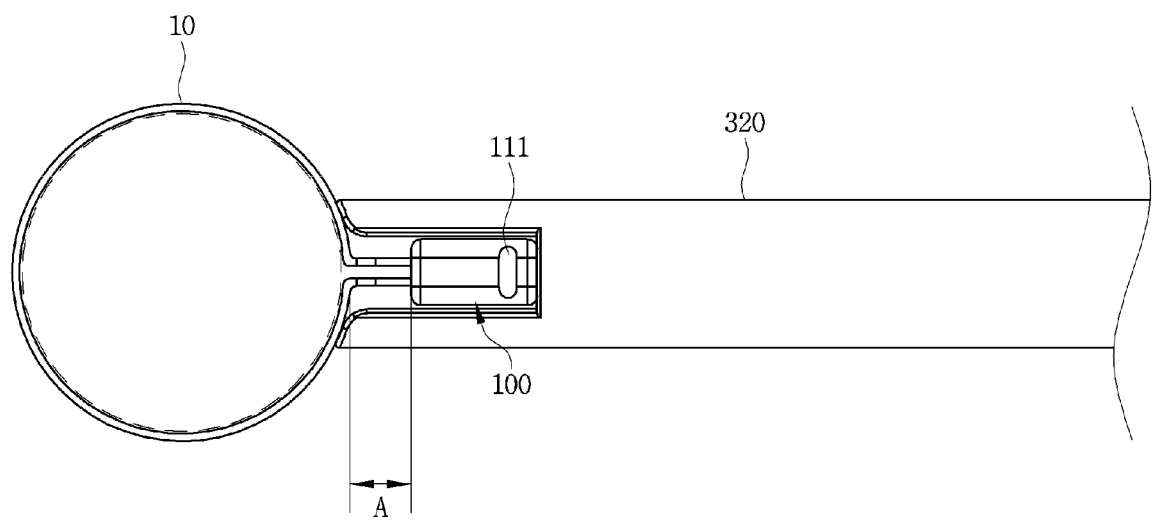
FIG. 19 is a view illustrating an exemplary operation and a reference distance, according to one embodiment of the present invention.

FIG. 18 is a view illustrating an exemplary operation according to one embodiment of the present invention, and FIG. 19 is a view illustrating an exemplary operation and a reference distance according to one embodiment of the present invention.

More specifically, FIG. 18 illustrates a state in which the pin fixing portions 25—are released from the respective recesses 111, the holder 200 is introduced into the accommodation space of the guide member 320, and the fixing pin 100 is blocked by the stepped portion.

In addition, referring to FIG. 18, in the process in which the holder 200 is introduced into the accommodation space of the guide member 320, the band 10 is also pulled toward the inside of the pulling member 300 (i.e., toward the inside of the guide member 320). Therefore, tensile stress is applied to the band 10 wound around the intestine 1. Thus, the band 10 is contracted to fit to the outer size of the intestine 1.

FIG. 19 illustrates a state in which the holder 200 is pulled toward the inside of the pulling member 300 so that the distance between the fixing pin 100 and the band 10 is adjusted to be a preset reference distance A. The reference distance A means a distance between the outer surface of the band 10 and the fixing pin 100. This reference distance A ranges from 3 mm to 7 mm as described above. The range is determined such that the intestine can be surrounded by the band 10 during relaxation and contraction of the intestine 1.

In addition, as described above, since the exposed outer surface of the guide member 320 is curved, when the holder 200 is pulled into the pulling member 300, although the exposed surface of the guide member 320 comes into contact with the outer surface of the band 10 wound around the outer surface of the intestine 1, damage to the outer surface of the band 10 does not occur.

Figure 20:
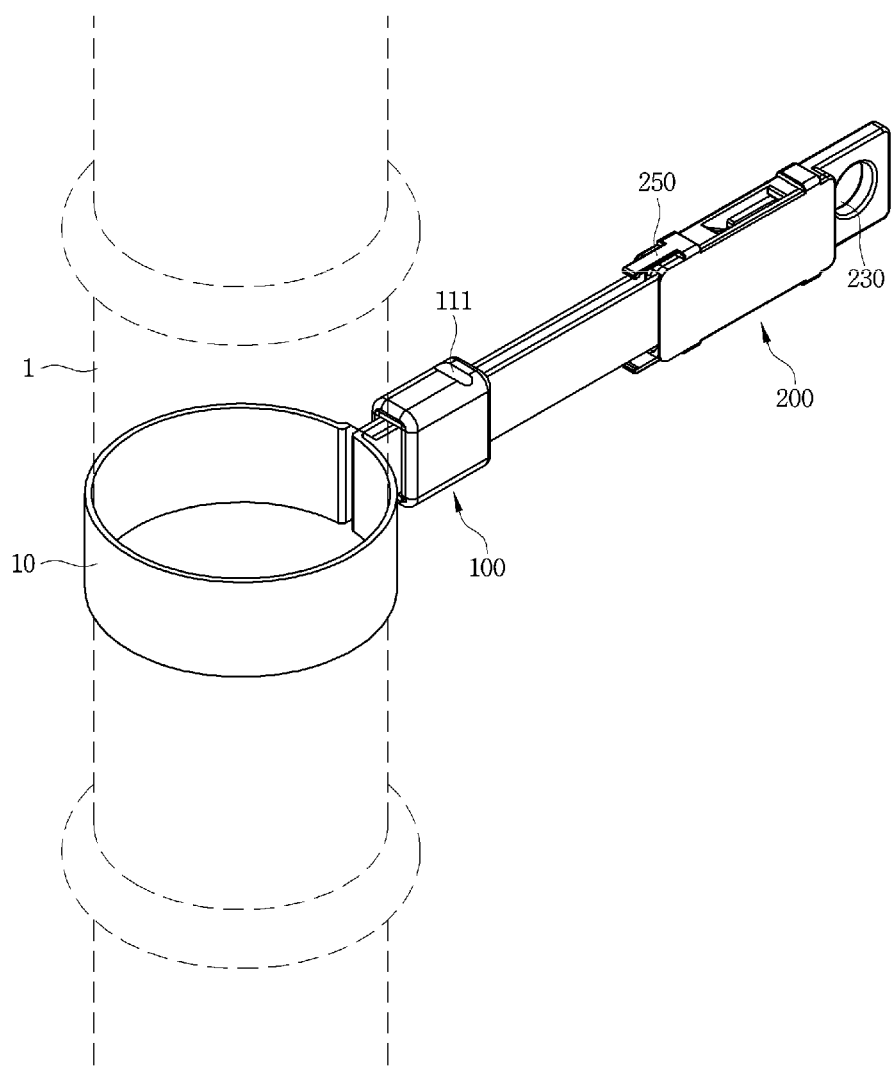
FIG. 20 is a view illustrating an exemplary operation according to one embodiment of the present invention.
Figure 21:
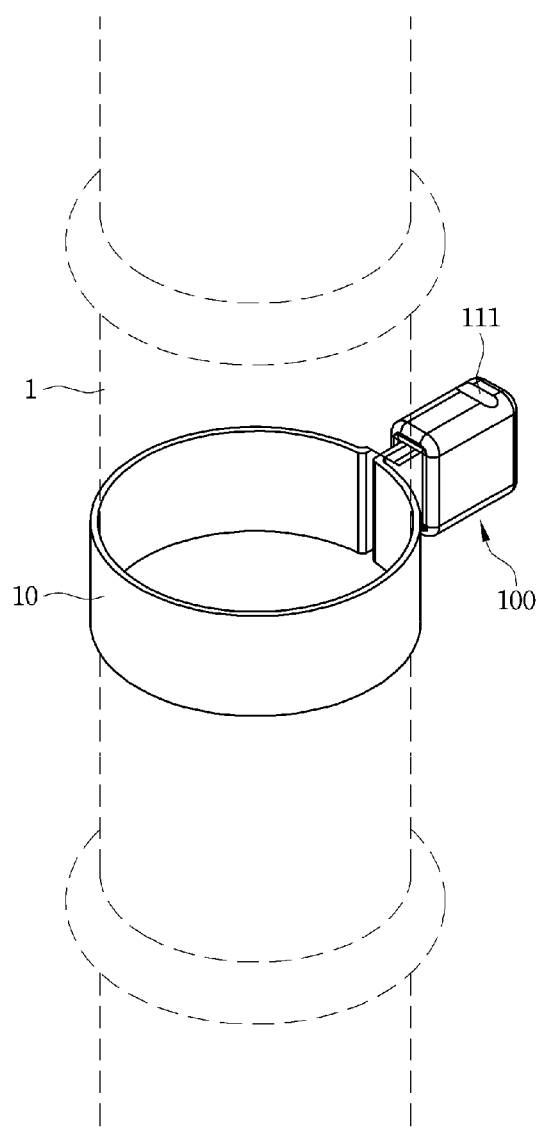
FIG. 21 is a view illustrating an exemplary operation according to one embodiment of the present invention.

FIG. 20 is a view illustrating an exemplary operation according to one embodiment of the present invention, and FIG. 21 is a view illustrating an exemplary operation according to one embodiment of the present invention.

FIG. 20 illustrates a case where the band 10 is wound around the intestine 1 to have an ideal tension, the fixing pin 100 and the holder 200 are separated from each other, and the hook 330 is disengaged from the loop 230. A portion of the band 10, which is positioned between the fixing pin 100 and the holder 200, is cut so that the band 10 can be wound with an ideal tension on the outer surface of the intestine 1.

FIG. 21 is a view illustrating a state in which the portion of the band 10, which is present between the fixing pin 100 and the holder 200, is cut away.

That is, referring to FIGS. 20 and 21, after the band 10 is fixed to the outer surface of the intestine 1 by the fixing pin 100, a specific portion of the band 10 (a portion present between the fixing pin 100 and the holder 200) can be cut with scissors or an ultrasonic cutting machine.

Figure 22A:
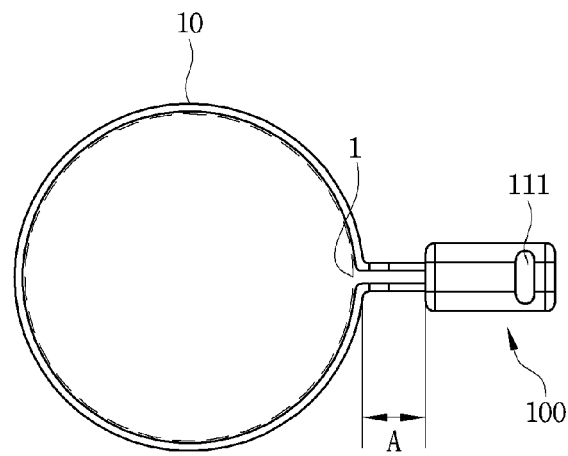
FIGS. 22a and 22b are views illustrating a change in shape of a band according to contraction and relaxation of an intestine.
Figure 22B:
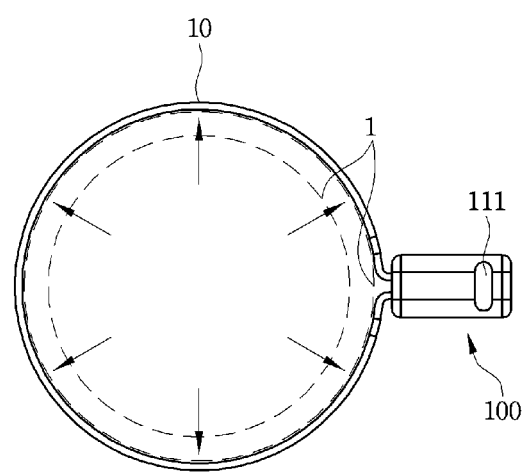

FIGS. 22a and 22b are views illustrating a change in shape of a band according to contraction and relaxation of an intestine.

Referring to FIGS. 22a and 22b, the intestine 1 contracts and relaxes. When the band 10 is wound around the outer surface of the intestine 1 without a reference distance secured between the fixing pin and the band, an optimum tension of the band 10 cannot be maintained during the contraction and relaxation of the intestine 1.

Therefore, as described above, by pulling the holder 200 toward the inside of the pulling member 300 so that the distance between the fixing pin 100 and the band 10 becomes a reference distance A which is, for example, in a range of 3 mm to 7 mm, the band 10 with an ideal tension can be wound around the intestine 1. Even during the relaxation of the intestine 1, the ideal tension of the band 10 can be maintained due to the presence of the gap between the fixing pin 100 and the band 10.

FIG. 22a illustrates a state in which the band 10 is wound around the outer surface of the intestine 1 that is contracted, and FIG. 22b illustrates a state in which the band 10 is wound around the outer surface of the intestine 1 that is relaxed.

Figure 23A:
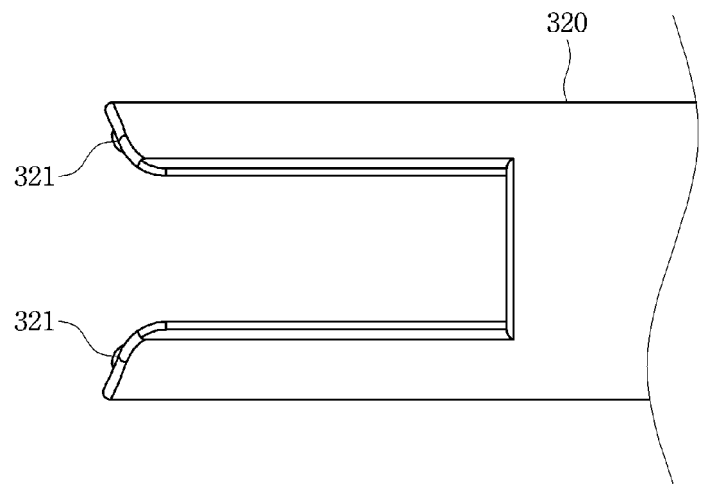
FIGS. 23a, 23b, and 23c are views illustrating a guide member provided with an anti-friction portion, according to another embodiment of the present invention.
Figure 23B:
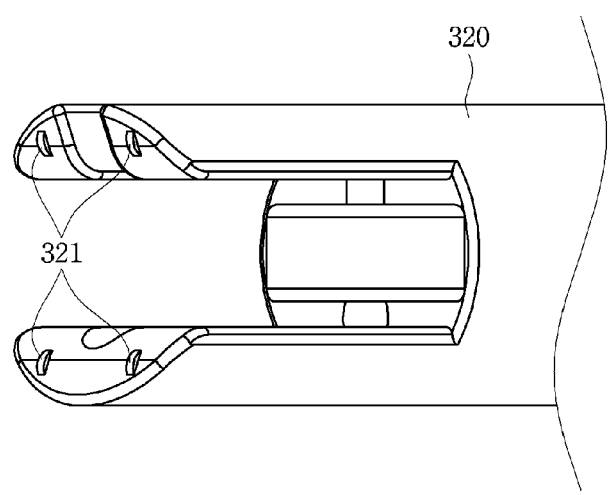
Figure 23C:
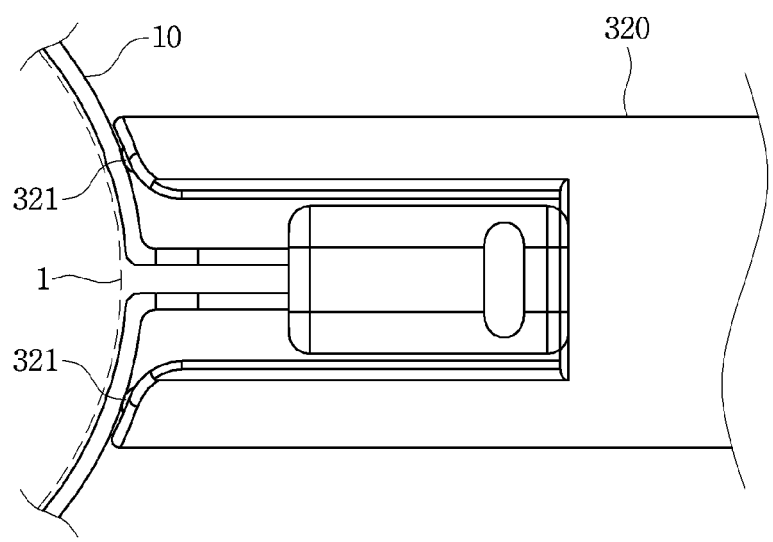

FIGS. 23a, 23b, and 23c are views illustrating a guide member provided with an anti-friction portion, according to another embodiment of the present invention.

Referring to FIGS. 23a, 23b, and 23c, FIG. 23a is side views illustrating a state in which the guide member 320 is provided with an anti-friction portion 321, FIG. 23b is a perspective view illustrating a state in which the guide member 320 is provided with the anti-friction portion 321, FIG. 23c is an operational view in which the guide member 320 is provided with the anti-friction portion 321. The anti-friction portion 321 prevents friction between the band 10 and the guide member 320.

More specifically, one surface of the guide member 320 is open, an outer surface of the guide member is a curved surface, and the anti-friction portion 321 is disposed on the outer surface of the guide member 320.

The anti-friction portion 321 is implemented with a wheel or irregularities. Thus, the friction between the outer surface of the band 10 and one surface of the guide member 320 is minimized.

Here, the number of the anti-friction portions 321 is one or more. That is, the number of the anti-friction portions is not limited to four although four anti-friction portions are illustrated in FIGS. 23a to 23c.

By minimizing the friction between the outer surface of the band 10 and one surface of the guide member 320, it is possible to prevent the band 10 wound around the intestine is insufficiently tightened.

As described above, the construction and operation of the band tightening apparatus for intestinal binding according to the present invention have been described with reference to various embodiments. Although specific embodiments have been described in the description of the present invention, various modifications thereto are possible without departing from the scope of the present invention.

While the present invention has been described with reference to specific exemplary embodiments and the drawings, it is apparent that the present invention is not limited to the disclosed exemplary embodiments, and it will be appreciated by those skilled in the art that various modifications and changes are possible.

It will be understood by those skilled in the art that various changes in form and details may be made without departing from the spirit and scope of the invention as defined by the appended claims. Therefore, the disclosed methods should be considered from an illustrative point of view, not from a restrictive point of view. The protection scope of the present invention should be construed as defined in the following claims, and it is apparent that all technical ideas equivalent thereto also fall within the scope of the present invention.

What is claimed is:

1. A band tightening apparatus for binding an intestine with a band, the apparatus comprising:
    a band having an elongated shape;
    a fixing pin having a passage-providing unit through which one end of the band passes;
    a holder configured to be assembled with and disassembled from the fixing pin and configured to fix one end of the band; and
    a pulling member configured to move the holder,
    wherein the band is wound to surround an outer surface of an intestine and a second end of the band is passed through a passage of the passage-providing unit and is fixed to the holder.

2. The apparatus according to claim 1, wherein the pulling member pulls the holder toward the inside of the pulling member so that a distance between the fixing pin and the band is adjusted to a preset reference distance.

3. The apparatus according to claim 1, wherein the pulling member includes a guide member along which a hook moves.

4. The apparatus according to claim 1, wherein the holder has pin fixing portions at respective side edges thereof, and
    the pin fixing portions are separated from the fixing pin when the pulling member applies a pulling force thereto.

5. The apparatus according to claim 1, wherein the holder includes a band fixing portion that fixes both ends of the band.

6. The apparatus according to claim 1, wherein the fixing pin restricts a direction in which the band moves such that the band moves only toward the inside of the pulling member.

7. The apparatus according to claim 2, wherein the reference distance is in a range of 3 mm to 7 mm.

8. The apparatus according to claim 3, wherein the guide member has an elongated opening formed along a longitudinal direction, and an outer surface of the guide member is a curved surface.

9. The apparatus according to claim 3, wherein the guide member is an elongated member so that the hook moves along a longitudinal direction of the guide member.

10. The apparatus according to claim 3, wherein a pressure sensor that measures a pulling force of the hook when the hook pulls the holder is disposed in the pulling member.

11. The apparatus according to claim 3, wherein an inner surface of the guide member locally differs in height.

12. The apparatus according to claim 4, wherein the pin fixing portions fix the fixing pin by pressing respective sides of the fixing pin, and wherein when the holder is pulled toward the inside of the pulling member such that a tension is applied to the fixing pin, the pin fixing portions are separated from the fixing pin.

13. The apparatus according to claim 5, wherein the band has notches at respective side edges thereof;
    the band fixing portion has protrusions corresponding to the respective notches; and
    the protrusions are fitted into the respective notches so that the band is fixed.

14. The apparatus according to claim 6, wherein the fixing protrusions protrude from an inner surface of the fixing pin and are inclined, and the fixing protrusions fix the band such that the band is moved toward the pulling member and is not moved outward from the pulling member.

* * * * *